United States Patent [19]

Braynin et al.

[11] Patent Number: 5,122,284

[45] Date of Patent: Jun. 16, 1992

[54] APPARATUS AND METHOD FOR OPTICALLY ANALYZING BIOLOGICAL FLUIDS

[75] Inventors: Boris Braynin, Mountain View; Tammy L. Burd, Fremont; Vladimir Ostoich, Los Altos, all of Calif.

[73] Assignee: Abaxis, Inc., Mountain View, Calif.

[21] Appl. No.: 678,824

[22] Filed: Apr. 1, 1991

Related U.S. Application Data

[63] Continuation-in-part of Ser. No. 532,524, Jun. 4, 1990.

[51] Int. Cl.⁵ .................. B01D 21/26; G01N 21/07
[52] U.S. Cl. ..................... 210/782; 210/745; 210/789; 210/94; 210/198.1; 210/380.1; 210/514; 210/532.1; 356/246; 356/427; 422/72; 422/102; 436/45; 436/63; 436/177; 436/180; 494/10; 494/17; 494/29; 494/37; 494/43
[58] Field of Search .............. 210/94, 95, 198.1, 380.1, 210/407, 512.1, 514, 515, 532.1, 745, 782, 787, 789; 422/64, 72, 101, 102; 436/45, 63, 177, 180; 494/16, 17, 27, 29, 37, 43, 10; 356/246, 427

[56] References Cited

U.S. PATENT DOCUMENTS

| Re. 31,149 | 2/1983 | Ginsberg et al. | 422/64 |
|---|---|---|---|
| 3,982,838 | 9/1976 | Thacker | 356/225 |
| 4,154,793 | 5/1979 | Guigan | 422/72 |
| 4,226,537 | 10/1980 | Colley | 356/427 |
| 4,350,283 | 9/1982 | Leonian | 233/26 |
| 4,412,973 | 11/1983 | Gugan | 422/72 |
| 4,431,307 | 2/1984 | Suovaniemi | 356/246 |
| 4,469,793 | 9/1984 | Gugan | 436/45 |
| 4,509,856 | 4/1985 | Lee | 356/246 |
| 4,623,519 | 11/1986 | Cornut et al. | 422/72 |
| 4,652,137 | 3/1987 | Calzi | 356/427 |
| 4,695,164 | 9/1987 | Zivitz et al. | 356/427 |
| 4,762,683 | 8/1988 | Romanauskas | 422/72 |
| 4,776,697 | 10/1988 | Kamrat | 356/336 |
| 4,785,407 | 11/1988 | Sakagami | 364/497 |
| 4,837,160 | 6/1989 | Meserol et al. | 436/45 |
| 4,894,204 | 1/1990 | Cornut | 422/72 |

*Primary Examiner*—W. Gary Jones
*Attorney, Agent, or Firm*—Townsend and Townsend

[57] ABSTRACT

A centrifugal rotor comprising a plurality of peripheral cuvettes and a collection chamber spaced radially inward from the cuvettes is disclosed. The rotor includes a means for introducing fluid into the collection chamber and plurality of generally radial inlet channels connecting each cuvette to the chamber. Each inlet channel has a discrete flow path for fluid to enter the cuvette and another discrete flow path for gas to exit the cuvette as the cuvette is filled. Positioned radially inward from each cuvette is a reflective surface capable of deflecting a light beam from a generally vertical direction to a generally horizontal direction or vice versa. As the rotor is spun, fluid enters the cuvettes from collection chamber through the inlet channels, which also allow gas in the cuvettes to escape, thus avoiding the creation of bubbles in the cuvette after the cuvettes are filled. The contents are then optically analyzed by passing a light beam horizontally through the cuvette.

25 Claims, 2 Drawing Sheets

APPARATUS AND METHOD FOR OPTICALLY ANALYZING BIOLOGICAL FLUIDS

This application is a continuation-in-part of copending application Ser. No. 07/532,524, filed Jun. 4, 1990, which is incorporated herein by reference. The present invention is related to the inventions disclosed in copending applications Ser. No. 07/678,823, and Ser. No. 07/678,762, both of which are incorporated herein by reference.

BACKGROUND OF THE INVENTION

1. Field of the Invention

The present invention relates generally to devices and methods for optically analyzing biological fluids. In particular, it relates to the design and use of centrifugal rotors which allow peripheral cuvettes to be filled, without creation of air bubbles, as the rotor spins and the subsequent rapid optical analysis of the fluid in each cuvette.

Blood plasma and other biological fluids or material frequently require that liquids be quickly divided into a plurality of discrete aliquots so that a variety of optical tests or assays may be performed. It is also frequently desirable to first separate potentially-interfering cellular components of the material from the biological fluid prior to testing. Such separation and division steps have heretofore been typically performed by centrifugation to separate, for instance, blood plasma from the cellular components, followed by manual or automated pipetting of the blood plasma into separate test wells. Such procedures are labor intensive and time-consuming, and various automated systems and methods have been proposed for providing multiple aliquots of plasma suitable for testing in a more efficient manner.

Of particular interest to the present invention are centrifugal rotors which have been modified both to separate plasma from whole blood and to then distribute the separated plasma into separate test wells which are suitable for optically analyzing their contents. The use of such rotors can provide a plurality of discrete plasma volumes, and/or diluted plasma volumes which may be tested or evaluated, all present within the centrifugal rotor, greatly enhancing the efficiency of automated testing procedures.

Although a significant improvement over prior manual or partly manual procedures, previous modified centrifugal rotors have suffered from a number of deficiencies. Such rotors have frequently required the application of relatively large volumes of whole blood or other biological material in order to achieve the desired separation and distribution. The rotors are also not well designed for optical analysis of the contents of the individual test wells. Those rotors that allow optical analysis in situ require that the light beam pass vertically through the test well. Thus, variations in the amount of fluid in each well leads to variation in the length of the light path and can lead to variable results in the assays. In addition, without reliable methods for evacuating gas from the test wells, air bubbles introduced into the wells during filling can also affect analysis. Such air bubbles are particularly disadvantageous when optical analysis is performed using light beams passing vertically through the rotor.

Moreover, prior art rotors have frequently utilized complex designs which are difficult and costly to manufacture. Often, the rotors require various separable parts or components which are brought together or separated at different points in the centrifugation procedure. Previous centrifugal rotors have often been limited in the number of discrete samples and test wells which they can provide, and in some cases require the use of a separate displacement fluid to effect flow of blood and plasma through the system.

For these reasons, it would be desirable to provide improved centrifugal rotors and methods suitable for separating biological materials into fluid and cellular components, diluting the fluid, if necessary, and further distributing the fluid into a plurality of discrete cuvettes within the rotors. The rotors should be capable of separating and distributing relatively small volumes of fluid and should not require the use of a displacement fluid for effecting such separation. Moreover, to decrease variability between assays, the cuvettes should provide a uniform light path and should not contain air bubbles after filling.

The rotors should be able to accommodate relatively large numbers of test wells, and the rotor design should be simple and amenable to low-cost manufacturing procedures. In particular, it would be desirable if the rotors were of unitary construction with no separable or movable parts. Plasma separation methods should be simple and be capable of being performed in relatively short times. In particular, the methods should require relatively few steps and should be capable of being performed with little or no intervention or manipulations by the operator. It would be particularly desirable if the methods required only rotation of the rotor in order to effect distribution of the fluid into the cuvettes, followed by optical analysis in situ.

2. Description of the Background Art

U.S. Pat. No. 4,623,519 describes a centrifugal rotor which comprises a liquid feed and gas evacuating duct which depends on the rough surfaces of the duct to create random patterns by which fluid enters the test well and gas escapes. The liquid feed and gas evacuating flow paths are not discrete U.S. Pat. Nos. 4,154,793 and 4,762,683 relate to centrifugal rotors having peripheral cells, each cell having a separate air escape orifice to allow air to escape as the cell is filled with liquid. U.S. Pat. No. 4,412,973 discloses a centrifugal rotor having peripheral cells which are fed by two separate paths for conveying liquid to the cell. One path being for the sample, the other for reagents. U.S. Pat. Nos. 4,469,793 and 4,894,204 relate to centrifugal rotors which dispense a predetermined dose of a sample liquid into a peripheral cell on the rotor.

U.S. Pat. No. 4,652,137 relates to a centrifugal rotor comprising an array of peripheral cuvettes, the contents of which are optically analyzed using a vertical light source and detector. U.S. Pat. No. 4,695,164 describes a position detector for detecting a rotational position of a rotor of a centrifugal analyzer wherein the light beam is deflected by mirrors that are not on the rotor. U.S. Pat. No. 4,226,537 relates to an analytical centrifuge having mirrors which deflect a light beam. The mirrors are not on the rotor. U.S. Pat. Nos. 4,785,407 and Reissue No. 31,149 relate to carousel analyzers, the cuvettes of which are optically analyzed. Reissue U.S. Pat. No. 31,149 discloses the use of mirrors to deflect the light beam, the mirrors are not a part of the rotating carousel. U.S. Pat. No. 4,431,307 relates to a set of cuvettes which are adapted to optical analysis using a vertical light source and detector. U.S. Pat. No. 4,776,697 relates to an optical particle analyzer. U.S. Pat. No. 4,350,283 relates to a centrifuge rotor adapted for continuous separation of particles.

SUMMARY OF THE INVENTION

Figure 1:
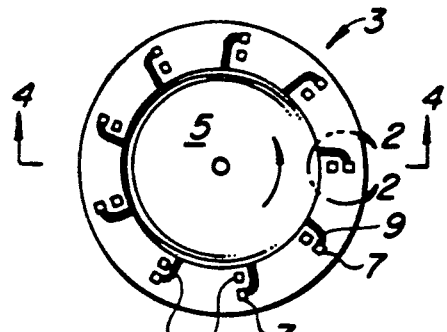
FIG. 1 is a plan view of the bottom layer of a rotor made in accordance with the present invention.
Figure 2:
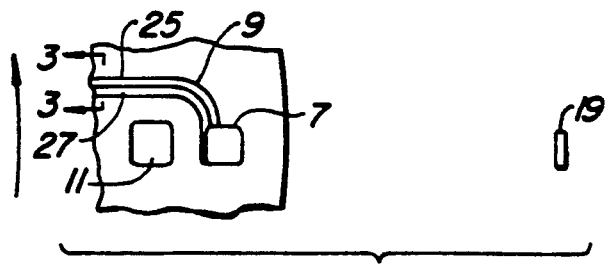
FIG. 2 is a plan view of the bottom layer of the rotor of FIG. 1 showing a cuvette, a curved inlet channel and a reflective surface.
Figure 4:
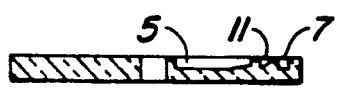
FIG. 4 is a cross-sectional view along line 4—4 of the bottom layer of the rotor in FIG. 1.

The present invention relates to a centrifugal rotor comprising a plurality of peripheral cuvettes, each of which is connected to a central collection chamber by means of a generally radial inlet channel which has a discrete flow path for flow of liquid into the cuvette and a second discrete flow path for flow of gas out of the cuvette as the rotor is spun. Preferably, the liquid flow path is on the side of the inlet channel in the direction of the rotation of the rotor and the gas evacuation flow path is on the side away from the direction of the rotation. The liquid is channeled into its flow path by differences in depth or surface texture between the two flow paths.

The rotor is typically used to analyze whole blood, the cellular components of which are first separated from the plasma. This is preferably done using a separation chamber having a cell trap disposed above the collection chamber in the rotor. An axial drainage port allows the separated plasma to flow into the collection chamber from the separation chamber.

The rotor also comprises a plurality of reflective surfaces positioned radially inward from the cuvettes, the reflective surfaces being capable of deflecting a light beam by about 90°. Typically, a light beam oriented generally parallel to the axis of rotation of the rotor is deflected so that it passes horizontally through a fluid in the cuvette. The reflective surface is preferably oriented at about a 45° angle to the vertical axis of the rotor and is produced by a total internal reflection condition at the rotor material/air interface.

The rotor of the present invention is preferably made of clear plastic, more preferably acrylic. Each cuvette typically contains reagents necessary for a biochemical analysis of the fluid in the cuvette. The biochemical analysis preferably produces an optical effect when exposed to the light beam which is then detected and analyzed.

Other advantages of the subject invention will be apparent to those skilled in the art from consideration of the detailed description of embodiments of the subject invention set forth below and of the attached drawings.

DESCRIPTION OF THE SPECIFIC EMBODIMENTS

The present invention provides devices and methods for optically analyzing biological fluids, and in particular for analyzing blood plasma after first separating it from cellular material in a centrifugal rotor. The apparatus and methods provide for distribution of the separated plasma or diluted plasma into a plurality of cuvettes within the rotor so that different optical analytic procedures may be performed without having to transfer aliquots of the fluid from the apparatus. Conveniently, the present invention decreases variability in the analyses by providing uniform optical paths in each cuvette and avoiding the creation of air bubbles when filling the cuvette. Uniform optical paths are provided through the use of reflective surfaces in the rotor which deflect a light beam oriented parallel with the axis of cuvette. Alternatively, a horizontal (e.g., radial) light beam may be deflected vertically after passing through the fluid. Using either embodiment, variations in the amount of fluid in the cuvette, distortions in the light path due to welding seams, or matter floating on the top of the fluid will not affect results. The creation of air bubbles is also avoided by the use of novel inlet channels which allow gas to exit through one flow path in the channel, while fluid enters through another flow path in the same channel.

The apparatus is very easy to manufacture and can be produced at a very low cost, making the apparatus suitable for use as a disposable in testing whole-blood samples. The apparatus can provide for automatic combination of the separated plasma with a reagent or diluent and can apportion substantially equal volumes of plasma among the plurality of cuvettes. More importantly, the apparatus is suitable for use with a variety of conventional analytic measurement devices, such as spectrophotometers and fluorometers, which allow the plasma in the cuvettes to be individually examined without the need to remove the plasma from the rotor.

Although the present invention is particularly suitable for analyzing blood plasma or diluted blood plasma, it will be useful with a wide variety of other biological fluids, such as urine, sputum, semen, saliva, ocular lens fluid, cerebral fluid, spinal fluid, amniotic fluid, and tissue culture media, as well as food and industrial chemicals, and the like. Where it may be desirable to separate cells and other interfering substances prior to analysis or assay, the devices and methods described in copending, parent application, U.S. Ser. No. 532,524 are preferably used. That application discloses a centrifugal rotor for separating plasma from whole blood which includes a plurality of internal chambers and passages for combining the plasma with one or more reagents and distributing the plasma to a plurality of individual test wells. The chambers and passages necessary for separating the whole blood into plasma are located on a first, upper level within the rotor and include a measuring chamber, an overflow chamber, a separation chamber, and a reagent chamber. The measuring chamber and overflow chamber have capillary dimensions so that an initial volume of whole blood partitions therebetween, with the measuring chamber filling first to provide a preselected volume. The separation chamber is located radially outward from both the measuring chamber and the reagent or diluent chamber so that spinning of the rotor causes both the reagent and the measured blood volume to flow outward into the separation chamber. The separation chamber includes a radially-outward cell trap and a radially-inward drainage port so that spinning of the rotor causes the cellular components of the whole blood to enter the cell trap, while cessation of spinning allows the separated plasma to flow downward through the drainage port. A collection chamber is formed at a lower level than the rotor to receive the plasma through the drainage port. It is not necessary, however, that the collection chamber be positioned below the separation chamber. For instance, the collection chamber and the cuvettes used for optical analysis can also be on the same level as the separation chamber and measuring chamber. Fluid can flow from the separation chamber to the collection chamber by gravity, inertial, centrifugal, capillary force, or a combination of these forces.

The apparatus of the present invention includes a centrifugal rotor which is capable of being mounted on a conventional laboratory centrifuge of the type which is commercially available from suppliers, such as Beckman Instruments, Inc., Spinco Division, Fullerton, Calif.; Fisher Scientific, Pittsburgh, Penna.; VWR Scientific, San Francisco, Calif., and the like. Generally, the centrifugal rotors will include a receptacle or other coupling device suitable for mounting on a vertical drive shaft within the centrifuge. The particular design of the receptacle or coupling device will depend on the nature of the centrifuge, and it will be appreciated that the centrifugal rotor of the present invention may be adapted to be used with most types of centrifuges which are now available or which may become available in the future so long as the velocity profile can be programmed.

The centrifugal rotor comprises a body structure which maintains a desired geometric pattern or relationship between a plurality of cuvettes and interconnecting inlet channels, as described in more detail hereinbelow. Usually, the body will be a substantially solid plate with the chambers and passages formed as spaces or voids in an otherwise solid matrix. Conveniently, such solid plate structures may be formed by laminating a plurality of separately formed layers together into a composite structure where the chambers and passages are generally formed between adjacent layers. The individual layers may be formed by injection molding, machining, and combinations thereof, and will usually be joined together, typically using a suitable adhesive or by ultrasonic welding. The final enclosed volumes are formed when the layers are brought together. Of course, the centrifugal rotor could also be formed as a plurality of discrete components, such as tubes, vessels, chambers, etc., arranged in a suitable structural framework. Such assemblies, however, are generally more difficult to manufacture and are therefore less desirable than those formed in a substantially solid plate.

The centrifugal rotor may be formed from a wide variety of materials and may optionally include two or more materials. Usually, the materials will be transparent so that the presence and distribution of blood, plasma, and other reagents, may be observed within the various internal chambers and passages. Also, it is generally required that the test wells formed within the rotor have suitable optical paths formed therethrough so that the contents of the test well may be observed spectrophotometrically, fluorometrically, or by other optical assessment instruments. In the exemplary embodiment described below, the rotor is formed from acrylic resins having the required optical properties, at least in those areas which define the optical paths.

The apparatus and method of the present invention are suitable for performing a wide variety of analytic procedures which are beneficially or necessarily performed on blood plasma or diluted plasma. The analytic procedures will generally require that the blood plasma be combined with one or more reagents so that some optically detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamicoxaloacetic transaminase (SGOT), serum glutamic-pyruvic transaminase (SGPT), blood urea (nitrogen) (BUN), total protein, alkalinity, phosphatase, bilirubin, calcium, chloride, exhaustive and is intended merely as being exemplary of the assays which may be performed using the apparatus and method of the present invention. Usually, these tests will require that the blood plasma be combined with one or more reagents which result in a visually detectable, usually photometrically detectable, change in the plasma. The reagents which are required are well known and amply described in the patent and scientific literature.

Referring now to FIGS. 1-7, a cylindrical rotor 1 constructed in accordance with the principles of the present invention is shown in detail. The rotor 1 is in the form of a substantially solid disk, the bottom layer 3 of which is shown in FIG. 1. Typically, the bottom layer 3 is composed of a transparent plastic, such as acrylic. The bottom layer 3 comprises a sample collection chamber 5 spaced radially inward from a plurality of peripheral cuvettes 7. Each cuvette 7 is connected to the collection chamber 5 by an inlet channel 9. The collection chamber may be formed in any shape, for instance, as a circle, a ring, or the like.

Each inlet channel 9 comprises two discrete flow paths, a first flow path 25 for the flow of liquid into the cuvette 7 and a second flow path 27 for the flow of gas out of the cuvette. The term "discrete" as used herein refers to the fact that the two flow paths 25 and 27 are separately defined and distinct from each other. The inlet channels 9 are preferably curved so as to prevent backwash or carryover when the contents of the cuvettes are agitated to effect mixing of the contents. Thus, cross contamination between cuvettes is avoided. The use of the flow paths 25 and 27 allow gas to escape easily from the cuvette 7 as it is filled and thus prevent the formation of bubbles in the cuvette 7, which can deleteriously affect the results of optical analyses.

Figures 3A, 3B, 9:
FIGS. 3a and 3b shows two cross-sectional views along line 3—3 in FIG. 2.
FIG. 9 is a cross-sectional view along line 9—9 in FIG. 8.
Figure 5:
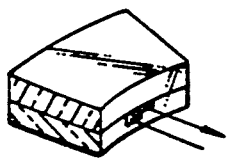
FIG. 5 is perspective view of an inlet channel showing the direction of flow in the discrete flow paths.
Figure 8:
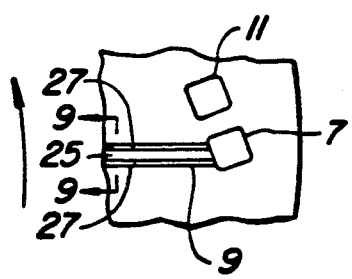
FIG. 8 is a plan view of the rotor showing a cuvette, a straight inlet channel and a reflective surface.

There are a number of ways to create two discrete flow paths in the inlet channel 9. For instance, FIGS. 3A, 3B, and 9 show three possible configurations in which liquid flow path 25 has a greater depth than the gas flow path 27. Because of its greater depth, the fluid will preferentially flow down path 25, leaving path 27 available for the evacuation of gas from the cuvette 9. The liquid flow path 25 may be on the side of the inlet channel 9 toward the direction of rotation of the rotor 1, as shown in FIGS. 3A and 3B. In this configuration, centrifugal force will urge the liquid along the "leading" wall. Alternatively, if the inlet channel is not curved, as shown in FIG. 8, the fluid flow path 25 may be in the center of the inlet channel 9, as shown in FIG. 9.

The inlet channel 9 is conveniently formed such that it passes around a reflective surface 11 (described more fully, below). If a reflective surface 11 is present, the inlet channel 9 will typically pass around the reflective surface 11 on the side in the direction of rotation of the rotor. In the absence of a reflective surface 11, the inlet channel may be formed in any other generally radial configuration.

Other embodiments of the present invention utilize inlet channels 9 having regions with different surface textures. For instance, the gas flow path 27 may be left unpolished, leaving a rough surface texture in that region, 1 while the fluid flow path 25 is polished. Alternatively, the liquid flow path 25 may be treated so as to be hydrophilic whereas the gas flow path is treated so as to be hydrophobic. The manner of treatment to make the surfaces hydrophilic or hydrophobic is well known in the art and need not be recited here. Any known surface treatment may be used as desired so long as it is chemically inert to the fluids passing through the inlet channel 9.

The rotor of this invention thus permits rapid filling of the cuvettes. Each cuvette is filled completely leaving little or no gas to interfere with subsequent optical analysis of the cuvettes contents.

Figure 6:
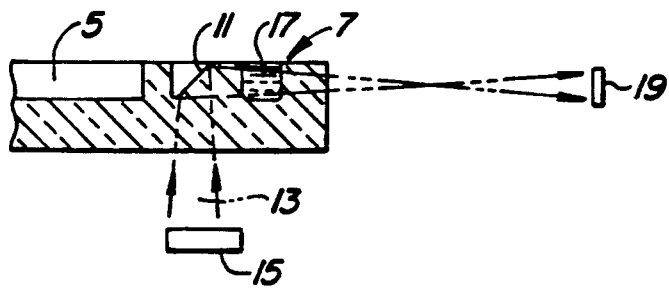
FIG. 6 is a cross-sectional view of the bottom layer of the rotor of the present invention showing the light path through the fluid in the cuvette.

Turning now to FIG. 6, it can be seen that optical analysis of the cuvette contents is facilitated by reflective surfaces 11 positioned radially inward from each cuvette 7 such that they are capable of deflecting a light beam between a generally vertical and a generally horizontal direction and which are oriented at about 45° from the vertical axis of the rotor. As used herein, the "horizontal" and "vertical" directions are determined in relation to the axis of rotation of the rotor. The horizontal direction (typically radial) is perpendicular to the axis and the vertical direction is parallel to the axis.

The reflective surface 11 need not be oriented directly radially inward from the cuvette. The reflective surface 11, however, must be parallel to the side of the cuvette in the optical pathway. For instance, a horizontal light beam which does not pass radially through the rotor may be used. Thus, the reflective surface 11 will be placed on a radial plane different from that of the cuvette 7, as shown in FIG. 8.

In an exemplified embodiment, the reflective surface deflects a vertical light beam 13 from a light source 15 so that it passes radially through a fluid 17 in the cuvette 7. A light is then detected by the detector 19. The orientation of the reflective surfaces 11 is such that the positions of the detector 19 and light source 15 can be reversed. In the reversed configuration a horizontal light beam passes through the cuvette contents and is then deflected so that it passes vertically through the rotor where it is detected below the rotor. The reflective surfaces can be composed of any reflective surface known in the art which provides total internal reflection, and are typically air mirrors in which light is reflected at the acrylic-air interface. Alternatively, the surface can be coated or backed with a light reflective material.

Figure 7:
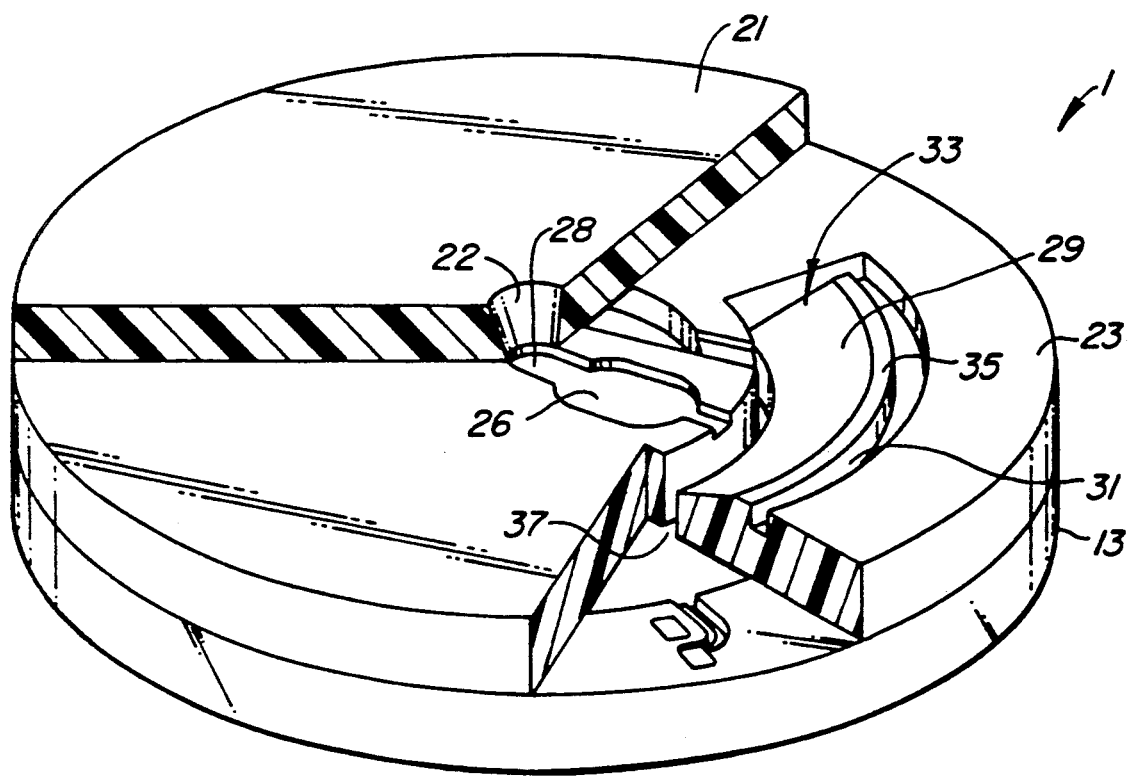
FIG. 7 is a perspective view, vertically sections showing the three layers of a rotor of the present invention.

Turning now to FIG. 7, the top layer 21 and the middle layer 23 are shown. These portions of the rotor separate the blood plasma from the cellular components before the plasma is distributed to the cuvettes. Like the bottom layer 13, they may be composed of a transparent material, such as acrylic. It is also possible that the layers are composed of different materials and that each layer will include two or more different materials forming different portions of the layer. As discussed above, the collection chamber 5 and cuvettes 7 can be positioned on the same level as the blood separation chambers.

The top layer 21 and middle layer 23 are typically as described in detail in the copending parent application. Briefly, these layers are as follows.

The top layer 21 includes a blood application port 22 which penetrates the entire thickness of the top layer 21 and is aligned with various chambers formed in the middle layer 23 of the rotor 1. The blood application port 22 may conveniently be formed in the top layer 21 by injection molding or machining, e.g., drilling.

The upper surface of middle layer 23 includes a plurality of chambers and passages formed therein. The chambers and passages may be formed by machining a disk having generally flat surfaces or may be formed by injection molding of a suitable plastic resin in order to initially form the disk.

The middle layer 23 includes a metering chamber 26 having an inlet segment 28 which is generally aligned with the blood application port 22 in top layer 21. The depth of metering chamber 26 will be selected to provide for capillary dimensions when the chamber are completed by lamination of the top layer 21.

A separation chamber 29 is formed in the upper surface of middle layer 23 and is disposed radially outward from the metering chamber 25. The separation chamber 29 includes a cell trap 31 formed at its radially-outward periphery and a receptacle region 33 formed along its radially-inward perimeter. A capillary region 35 is formed between the receptacle region 33 and the cell trap 31 in order to inhibit the backflow of cells after they have entered the cell trap 3 as a result of centrifugal separation. The receptacle region 33 provides a volume which is capable of receiving whole blood or other biological fluid (optionally combined with a diluent or reagent) and which retains the blood plasma or other separated fluid after centrifugation has been completed. An axial port 37 is conveniently formed as an annular passage which penetrates the entire thickness of middle layer 23 so that separated plasma may flow downward from receptacle region 33 of chamber 29 into the collection chamber 5 formed in bottom layer 3, as described above.

The above description of the embodiments of the invention and the attached drawings are provided by way of illustration only, numerous other embodiments will be apparent to one of skill in the art. Thus, limitations on the scope of the subject invention are to be found only in the claims set forth below.

What is claimed is:

1. A centrifugal rotor comprising a plurality of peripheral cuvettes, a collection chamber spaced radially inward from the cuvettes, a means for introducing a fluid into the chamber, and a plurality of generally radially inlet channels connecting each cuvette to the chamber, wherein each inlet channel comprises means for defining two contiguous flow paths, each flow path being separately defined and distinct, whereby the fluid enters the cuvette through a first flow path and gas exits the cuvette through a second flow path.

2. The rotor of claim 1, wherein the means for defining two contiguous flow paths comprises a first region having a smooth surface texture and a second region having a rough surface texture.

3. The rotor of claim 1, wherein the means for defining two contiguous flow paths comprises a first region having a greater depth than a second region.

4. The rotor of claim 1, wherein the means for defining two contiguous flow paths comprises a first region having a hydrophilic surface and a second region having a hydrophobic surface.

5. The rotor of claim 1, wherein the first flow path is on a side of the inlet channel in the direction of rotation of the rotor and the second flow path is on a side of the inlet channel away from the direction of the rotation of the rotor.

6. The rotor of claim 1, further comprising a separation chamber, having a cell trap, connected to the collection chamber.

7. The rotor of claim 6, wherein the collection chamber is disposed radially outward from the separation chamber.

8. The rotor of claim 1, wherein the fluid is blood plasma or diluted blood plasma.

9. The rotor of claim 1, wherein the rotor is formed from clear plastic.

10. The rotor of claim 1, wherein each cuvette contains reagents necessary for analysis of the fluid.

11. A centrifugal rotor comprising a plurality of peripheral cuvettes, a collection chamber spaced radially inward from the cuvettes and disposed below a separation chamber having a cell trap, an axial drainage port between the collection chamber and the separation chamber for introducing a biological fluid into the collection chamber, and a plurality of generally radial inlet channels connecting each cuvette to the collection chamber, wherein each inlet channel has a first discrete flow path for flow of the fluid into the cuvette as the rotor is spun and a second discrete flow path for flow of gas out of the cuvette as the rotor is spun.

12. A method for filling a peripheral cuvette in a centrifugal rotor with a fluid, the method comprising:
 introducing the fluid into a collection chamber disposed radially inward of the cuvette;
 spinning the rotor to effect the radially outward flow of the fluid through an inlet channel into the cuvette, wherein the inlet channel comprises means for defining two contiguous flow paths, each flow path being separately defined and distinct, whereby the fluid enters the cuvette through a first flow path and gas exits the cuvette through a second flow path.

13. A method of claim 12, further comprising separating the fluid from cellular material associated with the fluid before the step of introducing the fluid into the collection chamber.

14. A centrifugal rotor comprising a vertical axis, a plurality of peripheral cuvettes, and a plurality of reflective surfaces positioned radially inward from the cuvettes, wherein each reflective surface is oriented with respect to the vertical axis such that an incident light beam oriented generally parallel to the vertical axis is deflected to be oriented generally perpendicular to the vertical axis and an incident light beam oriented generally perpendicular to the vertical axis is deflected to be orientated generally parallel to the vertical axis.

15. The rotor of claim 14, wherein the reflective surface is oriented at about a 45 degree angle to the vertical axis of the rotor.

16. The rotor of claim 14, wherein the reflective surface is a mirror.

17. The rotor of claim 14, wherein at least a portion of the rotor comprises clear plastic.

18. The rotor of claim 17, wherein the clear plastic is acrylic.

19. The rotor of claim 14, wherein each cuvette contains reagents necessary for a biochemical analysis of the fluid.

20. The rotor of clam 19, wherein the biochemical analysis produces an optical effect when exposed to the light beam.

21. A rotor of claim 14, further comprising a collection chamber spaced radially inward from the cuvettes, a means for introducing the fluid into the chamber, and a plurality of generally radial inlet channels connecting each cuvette to the chamber, wherein each inlet channel comprises means for defining two contiguous flow paths, each flow path being separately defined and distinct, whereby the fluid enters the cuvette through a first flow path and gas exits the cuvette through a second flow path.

22. A method of optically analyzing a biological fluid in a centrifugal rotor having a vertical axis and a plurality of peripheral cuvettes, the method comprising:
 (a) placing the fluid in a collection chamber in the rotor;
 (b) spinning the rotor such that the fluid enters the cuvettes;
 (c) detecting a light beam after it has been reflected by a reflective surface oriented at about a 45 degree angle to the vertical axis.

23. The method of claim 22, wherein the light beam is oriented generally parallel to the vertical axis and is reflected to be oriented generally perpendicular to the vertical axis.

24. The method of claim 22, wherein the light beam is oriented generally perpendicular to the vertical axis and is reflected to be oriented generally parallel to the vertical axis.

25. A centrifugal rotor comprising a vertical axis, a plurality of peripheral cuvettes, a plurality of reflective surfaces oriented at about a 45 degree angle to the vertical axis and positioned radially inward from the cuvettes, a collection chamber spaced radially inward from the reflective surfaces, and a plurality of generally radially inlet channels connecting each cuvette to the chamber, wherein each inlet channel comprises means for defining two contiguous flow paths, each flow path being separately defined and distinct, whereby a fluid enters the cuvette through a first flow path and gas exits the cuvette through a second flow path.

* * * * *